(12) United States Patent  
Slingerland

(10) Patent No.: US 8,306,291 B2
(45) Date of Patent: Nov. 6, 2012

(54) METHOD FOR LOCALIZING LABELS IN A SAMPLE

(75) Inventor: Hendrik Nicolaas Slingerland, Venlo (NL)

(73) Assignee: FEI Company, Hillsboro, OR (US)

( * ) Notice: Subject to any disclaimer, the term of this patent is extended or adjusted under 35 U.S.C. 154(b) by 865 days.

(21) Appl. No.: 12/158,226

(22) PCT Filed: Dec. 22, 2006

(86) PCT No.: PCT/US2006/049177
§ 371 (c)(1),
(2), (4) Date: Jul. 15, 2008

(87) PCT Pub. No.: WO2008/045115
PCT Pub. Date: Apr. 17, 2008

(65) Prior Publication Data
US 2009/0220130 A1   Sep. 3, 2009

(30) Foreign Application Priority Data

Dec. 22, 2005 (EP) ..................................... 05112781

(51) Int. Cl.
*G06K 9/00* (2006.01)
(52) U.S. Cl. ...................................................... 382/128
(58) Field of Classification Search .......... 382/128–132
See application file for complete search history.

(56) References Cited

U.S. PATENT DOCUMENTS

| 5,435,850 | A | 7/1995 | Rasmussen |
| 5,698,397 | A | 12/1997 | Zarling et al. |
| 5,851,413 | A | 12/1998 | Casella et al. |
| 6,546,788 | B2 | 4/2003 | Magerle |
| 6,888,136 | B2 | 5/2005 | Geurts et al. |
| 6,984,491 | B2 | 1/2006 | Mirkin et al. |
| 6,992,760 | B2 | 1/2006 | Mohun et al. |
| 7,103,505 | B2 | 9/2006 | Teshima et al. |
| 7,312,448 | B2 | 12/2007 | Principe |
| 7,348,556 | B2 | 3/2008 | Chitturi et al. |
| 7,463,791 | B2 | 12/2008 | Koehler et al. |
| 7,474,986 | B2 | 1/2009 | Teshima et al. |
| 2006/0098188 | A1* | 5/2006 | Buijsse et al. .................. 356/72 |

(Continued)

FOREIGN PATENT DOCUMENTS

EP           1655597 A1      3/2005

(Continued)

OTHER PUBLICATIONS

Thiberge, S. et al. (2004) "Scanning electron microscopy of cells and tissues under fully hydrated conditions" PNAS vol. 101 No. 10, pp. 3346-3351.*

(Continued)

*Primary Examiner* — Courtney Thomas
(74) *Attorney, Agent, or Firm* — Scheinberg & Associates, PC; Michael O. Scheinberg

(57) ABSTRACT

The invention relates to a method in which labels are introduced in a sample, a flat surface is prepared on the sample and a series of images is made of the sample surface with e.g. a scanning electron microscope. The labels may be gold labels or e.g. fluorescent labels. By removing a surface layer between obtaining each image, labels at the surface in one image will be removed and will not be visible in a subsequent image. Thereby a 3D reconstruction of the position of labels in the sample can be made.

24 Claims, 1 Drawing Sheet

U.S. PATENT DOCUMENTS

Figure 1:
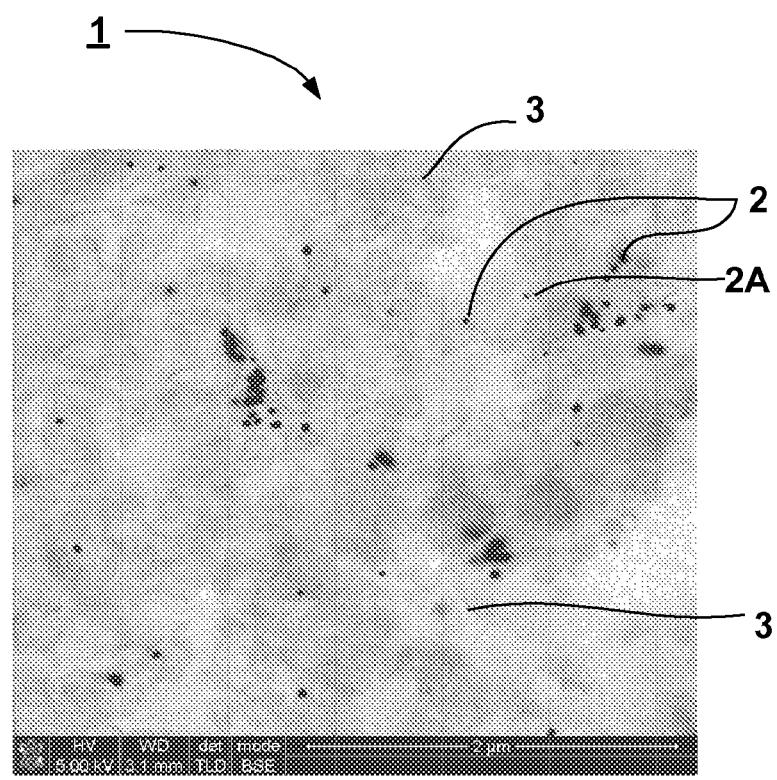

2009/0230303 A1    9/2009    Teshima et al.

FOREIGN PATENT DOCUMENTS

| EP | 1801593 | | 12/2005 |
| --- | --- | --- | --- |
| JP | 06-258578 | * | 9/1994 |
| JP | H06-258578 | | 9/1994 |
| JP | H08-115699 | | 5/1996 |
| JP | 2002-298774 | | 10/2002 |
| JP | 2003-246978 | | 9/2003 |

OTHER PUBLICATIONS

Shimizu, Daisaburo, et al., "Three-Dimensional Reconstruction by Scanning Electron Microscopy from Serial Epoxy Resin Semi-Thin Sections After Ion-Etching," Journal of Electron Microscopy, 2001, pp. 51-55, vol. 50.

Holzer, L. et al., "Three-Dimensional Analysis of Porous BaTiO3 Ceramics Using FIB Nanotomography," Journal of Microscopy, Oct. 2004, pp. 84-95, vol. 216, Pt. 1.

Steer, T.J. et al., "3-D Focused Ion Beam Mapping of Nanoindentation Zones in a Cu-Ti Multilayered Coating," Thin Solid Films, 2002, pp. 147-154, vol. 413.

Weninger, Wolfgang Johann et al., "Phenotyping Transgenic Embryos: a Rapid 3-D Screening Method Based on Episcopic Fluorescence Image Capturing," Nature Genetics, Jan. 2002 (Online Publication Dec. 17, 2001), 7 pgs.

Ewald, Andrew, et al., "Surface Imaging Microscopy, an Automated Method for Visualizing Whole Embryo Samples in Three Dimensions at High Resolution," Developmental Dynamics, 2002, pp. 369-375, vol. 225.

Frank, Joachim, "Electron Tomography, three-dimensional imaging with the transmission electron microscope," 1992, pp. 1-13.

Brandt, Sami, et al., 'Automatic Alignment of Electron Tomography Images Using Markers,' Proceedings of SPIE, 2000, pp. 277-287, vol. 4197.

Denk, Winfried, et al., 'Serial Block-Face Scanning Electron Microscopy to Reconstruct Three-Dimisional Tissue Nanostructure,' PLoS Biology, Nov. 2004, pp. 1900-1909, vol. 2, No. 11.

Subramaniam, Sriram, 'Bridging the Imaging Gap: Visualizing Subcellular Architecture with Electron Tomography,' Current Opinion in Microbiology, Jun. 1, 2005, pp. 316-322, vol. 8, No. 3.

Stephan Thiberge et al., "Scanning electron microscopy of cells and tissues under fully hydrated conditions", Proceedings of the National Academy of Sciences of the United States of America 9, Mar. 2004, vol. 101(10), pp. 3346-3351.

P. Gonzalez-Melendi et al "3-D gold in situ labelling in the EM," The Planet Journal, 2002, vol. 29(2), pp. 237-243.

Heymann et al., "Site-specific 3D imaging of cells and tissues with a dual beam microscope", Journal of Structural Biology, Orlando, US, Jul. 2006, vol. 155(1), pp. 63-73.

C. Harrison et al., "Layer by layer imaging of diblock copolymer films with a scanning electron microscope", Polymer, Elsevier Science Publishers B.V., Jun. 1998, vol. 30(13), pp. 2733-2744.

Frank, Joachim, "Electron Tomography, three-dimensional imaging with the transmission electron microscope," 1992, pp. 39-60.

Scott, John E., et al., "Dermatan Sulphate-Rich Proteoglycan Associates with Rat Tail-Tendon Collagen at the D Band in the Gap Region," BioChem, J. (1981) 197, pp. 213-216.

Nagato Y. et al., "Observation on Backscattered Electron Image (BEI) of a Scanning Electron Microscope (SEM) in Semi-Thin Sections Prepared for Light Microscopy," Tokai Journal of Experimental and Clinical Medicine, vol. 8, No. 2, 1983, pp. 167-174.

JP2008-547648, Office Action Mail Date Jan. 4, 2012, 4 pages.

* cited by examiner

METHOD FOR LOCALIZING LABELS IN A SAMPLE

The invention relates to a method for analysing a sample, the method comprising:
- preparing a substantially flat surface on the sample,
- exposing the sample to a labelling agent containing labels, thereby introducing labels into the sample,
- obtaining a series of images of the sample,
- obtaining the relative position of the labels in each of the images thus obtained, and
- from the relative positions thus obtained, deriving a 3D reconstruction of the relative position of the labels, Such a method is known from electron tomography as described in e.g. "Electron tomography, three-dimensional imaging with the transmission electron microscope", edited by J. Frank, ISBN 0-306-43995-6, further to be referred to as J. Frank.

In biology and histology there is a need to determine the location of certain molecules, such as proteins, antibodies and nucleotides, in, for example, biological samples, so as to gain insight as to where and how certain processes occur in, for example, biological samples. Similar needs arise during the analysis of e.g. polymers.

In electron tomography, a thin sample is irradiated with an electron beam in a Transmission Electron Microscope (TEM), an instrument known per se. The electrons in a TEM typically have an energy of between 80 and 300 keV. The sample is sufficiently thin to be partly transparent to the electrons. Different parts of the sample show different transparencies, as a result of which the amount of electrons passing unhindered through the sample is place dependant. By making a series of images, where the sample is tilted between each of the images (a so-named tilt series), and collecting data from this series of images, a 3D reconstruction can be made of the sample.

To image certain structures in e.g. biological tissue so-called labels may be attached to certain molecules. These labels are characterized in that they show a high contrast and attach themselves very specifically to, for example, certain types of antibodies, without attaching themselves to other types of antibodies and other molecules. By detecting the position of the labels in the sample, the presence and localisation of, for example, the antibodies can then be determined.

As the interaction between the electrons passing through the sample and the atoms making up the sample is highly dependant on the number of protons Z of the atoms, especially local variations in atomic composition of the sample can be imaged in this way. As biological material comprises very little high-Z atoms, especially labelling with labels containing high-Z material is very effective. Such labels may be labels comprising a protein-gold complex, in which the gold is present as gold nanoparticles with a typical diameter of between 1 and 50 nm. Such labels are commercially available from e.g. Nanoprobes Inc., Yaphank, N.Y. 11980-9710, USA under the name NanoGold®.

Another labelling technique employs fluorescent labels. These labels emit fluorescent light, often with a very specific wavelength, in response to irradiation with light or irradiation with a beam of e.g. electrons. The photons so emitted can be detected with a photon detector, thereby indicating the presence of a label at that position. Examples of such fluorescent labels are e.g. so-named semiconductor quantum dots, commercially available from e.g. Evident Technologies, Troy, N.Y. 12180, USA, under the name EviTag®. Also organic fluorescent labels are known and widely used. Another type of (inorganic) labels is described in e.g. European Application EP05112781.

It is remarked that preparing a flat surface on the sample and exposing the sample to a labelling agent need not be done in this sequence: it is well possible to provide labels to the sample first and then prepare a flat surface. See e.g. "3-D gold in situ labelling in the EM", P. Gonzalez-Melendi et al., the Plant Journal (2002) Vol. 29(2), pages 237-243.

A disadvantage of electron tomography is that it can only be used for extremely thin samples, because the electrons must pass through the sample. Often a thickness of less than 1 μm or even less than 100 nm is needed, as shown in J. Frank, page 25, FIG. 2. To study a certain structure in e.g. a cell, the feature under investigation must be present in the sample. Structures that are larger than the thickness of the sample can thus not be studied in their entirety. An associated risk is the structure to be studied is altogether missing in the thin sample.

Another disadvantage of electron tomography is that many images of the sample must be made, resulting in a high total dose of electrons impinging on the sample. This high total dose causes damage of the sample, as described in J. Frank, chapter 3. To minimize the damage while performing electron tomography it is therefore often necessary to take measures to minimize this damage, e.g. working at low dose conditions -resulting in a poor signal-to-noise ratio in the images- and/or cooling the samples to cryogenic temperatures, e.g. the temperature of boiling nitrogen or even the temperature of boiling helium.

The invention aims to provide a method for locating labels in thicker samples than possible in the prior art method.

To that end the method according to the invention is characterized in that
- each of the images shows the sample in a substantially identical orientation, and
- a surface layer is removed from the sample between each successive image of the series of images, leaving a fresh surface layer substantially parallel to the flat surface initially formed.

By determining the position of the labels in each of the images $I_i$, the disappearance of a label can be detected. Assuming the label is present in image $I_i$, and not in the subsequent image $I_{i+1}$, the label was present in the layer removed between obtaining images $I_i$ and $I_{i+1}$. By slicing many layers from the sample, it can thus be determined in which layer each label is located, and a 3D reconstruction can be made.

Similarly, when a label becomes visible, this implies that the label came to the surface to such an extent that both excitation and detection are possible (in the case of luminescent labels) or that -in the case of labels containing high-Z material- that backscattered electrons emanating from the label could be detected. This is especially useful when detecting labels with a beam of energetic particles, such as electrons or ions, as the reach of such particles is often limited to e.g. 1 μm or less.

The invention also enables 3D reconstruction of the position of labels in a sample using a scanning electron microscope (SEM). Scanning electron microscopy is a technique known per se. In scanning electron microscopy a finely focused electron beam with a beam energy of e.g. between 1 and 50 kV is scanned over the surface of the sample. From the position where the beam impinges on the sample, secondary radiation, such as back-scattered electrons or photons, emanates, to be detected by appropriate detectors, such as a back-scattered electron detector or a photon detector. The signal of one or more detectors is used to construct an image of the surface of the sample. As the energy of the electrons is much lower, the damage to the sample is also greatly reduced.

It is remarked that a method where multiple images from a sample are retrieved and layers are removed in order to obtain a 3D reconstruction of a sample is known from U.S. Pat. No. 6,546,788 B2. The patent describes a method in which, with a microscope having a control to determine the topography of a sample, the topography of the sample is determined after each removal of a layer, and with a scanning probe microscopy (SPM) a property of the surface is determined, the property being e.g. conductivity, electron density, etc. As an alternative for the use of a SPM, the use of an optical microscope is also disclosed. As alternatives for the microscope determining the topography, phase interference microscopes, confocal laser microscopes and SPM's are disclosed.

The method of U.S. Pat. No. 6,546,788 B2 differs from the method of the invention in that U.S. Pat. No. 6,546,788 B2 specifically addresses the study of uneven surfaces, where the microscope is used to determine the topography and the SPM to determine the property of interest. It differs from the invention in that, for each layer, it makes use of the images obtained from at least two different components, each of which forms an image to be analysed: one for the topography and one for the property to be determined. It further does not disclose enhancing specific structures in the sample by the use of labels, nor does it disclose the use of a particle beam to determine the position of such a label.

In an embodiment of the method according to the invention, the labels are luminescent labels, the particle beam is a finely focused particle beam scanned over the surface of the sample and wherein the information comprises information proportional to the amount of light emitted from said labels in response to exposure to the particle beam.

By scanning a finely focused particle beam, e.g. an electron beam, over the sample, fluorescent labels will be excited. These labels will then emit photons, to be detected by a photon detector. This enables determination of the position of labels with a high resolution. At low beam energies a resolution of better than 25 nm has been demonstrated.

It is remarked that the resolution thus obtained may be less than the resolution of the particle beam itself, as the labels are also excited by the secondary particles -such as secondary electrons and back-scattered electrons- generated by the irradiation of the sample with the finely focused beam.

In a further embodiment of the method according to the invention, the luminescent labels are inorganic nanoparticles, said nanoparticles comprising a host lattice doped with luminescent activator ions acting as luminescent centres for said nanoparticles, and wherein obtaining an image comprises detecting the light emitted from said activator ions.

This type of luminescent labels is described in European Application EP05112781. An advantage of using this type of labels is that they are very resistant to irradiation with e.g. electrons and that very little photo bleaching (that is: deterioration of the luminescent properties) occurs.

In another embodiment of the method according to the invention, the luminescent labels are inorganic quantum dot nanoparticles.

In still another embodiment of the method according to the invention, the luminescent labels are organic labels.

Organic labels have been around for quite some time. Many different luminescent labels targeted to couple with specific molecules are known.

In another embodiment of the method according to the invention, the labels comprise high-Z material.

E.g. polymers and biological tissues are mainly made up from low-Z material such as carbon, hydrogen, oxygen, etc., and often comprise little or no high-Z material. Therefore labels comprising high-Z material will show excellent contrast, both when using a TEM (Transmission Electron Microscope) and when using a SEM (Scanning Electron Microscope).

In a further embodiment of the method according to the invention, the high-Z material comprises gold nanoparticles.

Labels comprising gold nanoparticles are well-known and are commercially available, e.g. under the name NanoGold®.

In still another embodiment of the method according to the invention, the gold nanoparticles are enhanced with silver or gold.

Enhancing contrast of gold nanoparticles when using electron microscopy by adding silver or gold to the nanoparticles already present in the sample is a technique known to the person skilled in the art.

In another embodiment of the method according to the invention, obtaining the image comprises processing a signal detected by a particle detector.

Particle detectors, such as the well-known Everhart-Thomley detector or Solid State Backscattered Electron Detector, can be used to detect secondary particles emanating from the sample. With the output of such a detector the image can be built.

Also a Gaseous Secondary Electron Detector can be used, specially suited to operate at pressures of about 1 to 25 mbar. This pressure is attractive as it allows observation of samples at a pressure equal to or higher than the equilibrium pressure of water. Such detectors and others, operating at such high pressures, may be used in e.g. an Environmental Scanning Electron Microscope (ESEM®) or Variable Pressure Scanning Electron Microscope (VP-SEM).

In yet another embodiment of the method according to the invention, obtaining the image comprises processing a signal detected by an X-ray detector.

Instead of detecting secondary particles generated in the sample, X-rays generated in the sample can be detected.

In still another embodiment of the method according to the invention, the one or more surface layers are removed using a particle beam.

Removing surface layers by sputtering the sample with a beam of particles, such as a beam of ions, is a technique known per se.

In a further embodiment of the method according to the invention, the particle beam is a finely focused beam.

Using a beam of e.g. ions, surface material can be milled from a sample. This method is often used in e.g. instruments with both an ion column, generating a finely focused ion beam, and an electron column, generating a finely focused electron beam. The electron beam may be used for the observation of the sample and for determining the position of the labels (be it fluorescent or high-Z material labels), the ion beam can be used to remove surface material from the sample. The use of such a finely focused beam that is scanned over the surface has proven to result in the removal of layers with a uniform thickness.

It is remarked that only a local portion of the surface may be removed, and that not a complete surface layer needs to be removed, in order to increase the speed with which the surface layer is removed.

It is also remarked that, as known to the person skilled in the art, the milling speed can be greatly enhanced by admitting certain fluids to the vicinity of the sample. What fluids to use is strongly dependant on the composition of the sample under investigation.

In another embodiment of the method according to the invention, the one or more surface layers are removed with a beam of electromagnetic radiation.

Removal of surface layers with light, e.g. light generated by a laser, is a known method.

In another embodiment of the method according to the invention the one or more surface layers are removed by sublimation.

As mentioned earlier, samples may be frozen to cryogenic temperatures to minimize damage to the sample, or to avoid deformation of the sample, leading to artefacts. Inventor found that the removal of very small layers is possible by sublimation. Sublimation can either be performed between obtaining images, but also sublimation while imaging is possible. In the latter case the removal of a surface layer takes place between obtaining an image, but is not limited to that period of time.

In yet another embodiment of the method according to the invention, the removal of the one or more surface layers is performed in-situ in a particle-optical apparatus.

Performing the method of the invention in-situ increases throughput time of the analysis, both because the chamber of such an instrument where the sample resides during inspection need not be evacuated as well as because the sample need not be repositioned.

The invention is now elucidated with figures, in which identical numerals indicate identical features.

To that end:

FIG. 1 schematically depicts a SEM image before a surface layer is removed.

Figure 2:
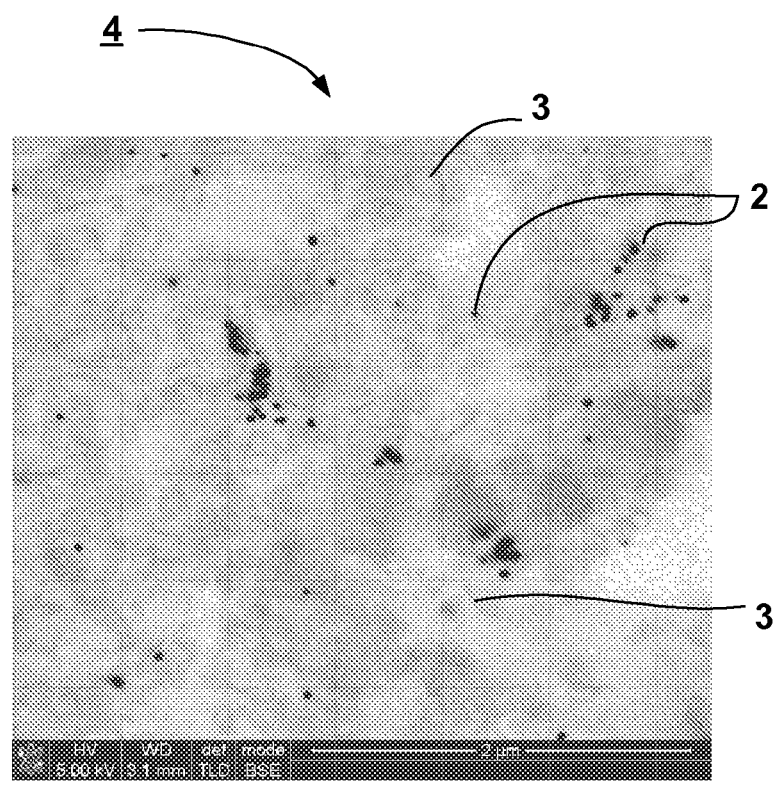

FIG. 2 schematically depicts a SEM image after a surface layer is removed.

FIG. 1 shows a SEM image of a biological sample. The sample is labelled with 2 nm gold labels, which were afterwards silver enhanced. The image shown is made using a 5 kV electron beam setting, while a back-scattered electron detector is used as detector.

In the image 1 the labels are shown as dark spots 2, 2A, of which several are indicated. Barely visible due to the low contrast are structures 3 in the sample.

FIG. 2 shows an image 4 of the same part of the sample as imaged after a thin surface layer is removed. Several labels disappeared, such as the label indicated with 2A in image 1 (FIG. 1). These labels are thus positioned in the layer removed between the first image 1 and the second image 4. In this way a 3D reconstruction of the position of the labels in the sample can be determined.

As can be seen in both images 1 and 4 some spots 2 are considerably larger than others. The inventor found that this is not due to a size difference in the labels, but that the larger dots represent labels which are deeper in the sample, in other words: more removed from the surface. This is probably due to the interaction volume of the electron beam in the sample, which is, as known to the person skilled in the art, more or less pear-shaped, showing a small diameter near the surface and a larger diameter deeper in the material. Thereby a label close to the surface, where the diameter of the interaction volume is small, will be detected with a higher resolution than a label further removed from the surface, where the diameter of the interaction volume is larger.

A surprising advantage of the method according to the invention is thus that an increased resolution can be obtained when the surface layers removed are smaller than the penetration depth of the particle beam, as in that case each label will sooner or later come close to the surface, where the diameter of the interaction volume is small.

It is remarked that similar images can be retrieved with a TEM or a STEM (Scanning Transmission Electron Microscope).

I claim:

1. A method for analysing a sample, the method comprising:
    preparing a substantially flat surface on the sample,
    exposing the sample to a labeling agent containing labels, thereby introducing labels into the sample,
    obtaining a series of images of the sample, each of the images comprising information of the sample, said information made available by exposing the sample to a beam of particles,
    obtaining the relative position of the labels in each of the images thus obtained, and
    from the relative positions obtained, deriving a 3D reconstruction of the relative position of the labels, wherein
    each of the images show the sample in a substantially identical orientation, and
    a surface layer is removed from the sample between each successive image of the series of images, leaving a fresh surface layer substantially parallel to the flat surface initially formed.

2. The method according to claim 1 in which the labels are luminescent labels, the particle beam is a finely focused particle beam scanned over the surface of the sample and wherein the information comprises information proportional to the amount of light emitted from said labels in response to exposure to the particle beam.

3. The method according to claim 2 in which the luminescent labels are inorganic nanoparticles, said nanoparticles comprising a host lattice doped with luminescent activator ions acting as luminescent centres for said nanoparticles, and wherein obtaining an image comprises detecting the light emitted from said activator ions.

4. The method according to claim 2 in which the luminescent labels are inorganic quantum dot nanoparticles.

5. The method according to claim 2 in which the luminescent labels are organic labels.

6. The method according to claim 1 in which the labels comprise high-Z material.

7. The method according to claim 6 in which the high-Z material comprises gold nanoparticles.

8. The method according to claim 7 in which the gold nanoparticles are enhanced with silver or gold.

9. The method according to claim 6 in which obtaining the image comprises processing a signal detected by a particle detector.

10. The method according to claim 6 in which obtaining the image comprises processing a signal detected by an X-ray detector.

11. The method according to claim 6 in which the one or more surface layers are removed using a particle beam.

12. The method according to claim 11 in which the particle beam is a finely focused beam.

13. The method according to claim 11 in which the one or more surface layers are removed with a beam of electromagnetic radiation.

14. The method according to claim 11 where the removal of the one or more surface layers is performed in-situ in a particle-optical apparatus.

15. The method according to claim 11 where an upper boundary of a label is determined based on the absence of the label in an image and the presence of the label in a subsequent image, and where a lower boundary of a label is determined based on the presence of the label in an image and the absence of the label in a subsequent image.

16. The method of claim 7 in which obtaining the image comprises processing a signal detected by a particle detector.

17. The method of claim 7 in which obtaining the image comprises processing a signal detected by a back-scattered electron detector.

18. The method of claim 7 in which obtaining the image comprises processing a signal detected by an X-ray detector.

19. The method of claim 8 in which obtaining the image comprises processing a signal detected by an X-ray detector.

20. The method claim 1 in which the one or more surface layers are removed using a particle beam.

21. The method of claim 1 in which the one or more surface layers are removed with a beam of electromagnetic radiation.

22. The method of claim 1 where the removal of the one or more surface layers is performed in-situ in a particle-optical apparatus.

23. The method of claim 1 where an upper boundary of a label is determined based on the absence of the label in an image and the presence of the label in a subsequent image, and where a lower boundary of a label is determined based on the presence of the label in an image and the absence of the label in a subsequent image.

24. A method for analysing a sample, the method comprising:
  preparing a substantially flat surface on the sample,
  exposing the sample to a labeling agent containing labels, thereby introducing labels into the sample,
  obtaining a series of images of the sample, each of the images comprising information of the sample, said information made available by exposing the sample to a beam of particles,
  obtaining the relative position of the labels in each of the images thus obtained, and from the relative positions obtained, deriving a 3D reconstruction of the relative position of the labels, wherein
  each of the images show the sample in a substantially identical orientation, and
  a surface layer is removed from the sample between each successive image of the series of images, leaving a fresh surface layer substantially parallel to the flat surface initially formed, the surface layers being removed by irradiating the surface and the removed layer being thinner than the penetration depth of the radiation.

* * * * *